US008219416B2

(12) United States Patent  
Auker et al.

(10) Patent No.: US 8,219,416 B2
(45) Date of Patent: *Jul. 10, 2012

(54) PATIENT BED SEARCH AND MANAGEMENT SYSTEM

(75) Inventors: Gerrit Dean Auker, Exton, PA (US); Vincent Anthony Buccellato, Chester Springs, PA (US); Robin J Grattan, West Chester, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 61 days.

This patent is subject to a terminal disclaimer.

(21) Appl. No.: 12/871,050

(22) Filed: Aug. 30, 2010

(65) Prior Publication Data

US 2010/0318378 A1   Dec. 16, 2010

Related U.S. Application Data

(63) Continuation of application No. 11/780,641, filed on Jul. 20, 2007, now Pat. No. 7,813,941.

(60) Provisional application No. 60/820,353, filed on Jul. 26, 2006.

(51) Int. Cl.
*G06Q 10/00* (2012.01)
*G06Q 50/00* (2012.01)

(52) U.S. Cl. .............................. 705/2; 705/3

(58) Field of Classification Search ................. 705/2, 3; 707/100

See application file for complete search history.

(56) References Cited

U.S. PATENT DOCUMENTS

| 4,135,241 | A | 1/1979 | Stanis et al. | |
| 7,539,623 | B1 | 5/2009 | Wyatt | |
| 7,716,066 | B2 | 5/2010 | Rosow et al. | |
| 7,720,695 | B2 | 5/2010 | Rosow et al. | |
| 7,734,479 | B2 | 6/2010 | Rosow et al. | |
| 7,756,723 | B2 | 7/2010 | Rosow et al. | |
| 7,774,215 | B2 | 8/2010 | Rosow et al. | |
| 2003/0074222 | A1* | 4/2003 | Rosow et al. | 705/2 |
| 2004/0128168 | A1 | 7/2004 | Wyatt | |
| 2004/0243446 | A1 | 12/2004 | Wyatt | |
| 2005/0010441 | A1 | 1/2005 | Wheeler | |
| 2005/0071198 | A1* | 3/2005 | Krupa | 705/2 |
| 2006/0247948 | A1 | 11/2006 | Ellis et al. | |

(Continued)

OTHER PUBLICATIONS

Bed Tracking HTTP://WWW.TELETRACKING.COM/SOLUTIONS/BedTracking/INDEX.CFM.

(Continued)

*Primary Examiner* — Luke Gilligan
(74) *Attorney, Agent, or Firm* — Alexander J Burke (57) ABSTRACT

An automated search system uses data indicating clinical and non-clinical needs of a patient to provide a ranked list of candidate beds, status of beds and availability of a specific type of bed having a particular set of clinical attributes, using a score value derived using configurable rules for comparing patient requirements with bed characteristics. A patient bed search system includes at least one repository including bed information for multiple beds in a healthcare facility comprising multiple clinical attributes including current availability for individual beds of the multiple beds. A bed management processor automatically employs the bed information in providing data representing a candidate list of beds for a particular patient in response to clinical and non-clinical requirements associated with the particular patient and a request to allocate a bed for the particular patient. A user interface generates data representing at least one display image presenting the candidate list of beds for a particular patient.

21 Claims, 7 Drawing Sheets

U.S. PATENT DOCUMENTS

2007/0129983 A1 6/2007 Scherpbier et al.
2008/0109255 A1* 5/2008 Allen et al. .................. 705/2
2009/0119127 A2 5/2009 Rosow et al.

OTHER PUBLICATIONS

The Bed Management Suite http://www.teletracking.com/solutions/BedTrackingmobile/index.cfm.

PreAdmitTracking http://www.teletracking.com/solutions/PreAdmitTracking/index.cfm.
TransportTracking http://www.teletracking.com/solutions/transportTracking/index.cfm.
ServiceTracking http://www.teletracking.com/solutions/workOrderTracking/index.cfm.
PateintTrackingOR http://www.teletracking.com/solutions/Patient-TrackingOR/index.cfm.

* cited by examiner

FIGURE 1

SELECT A BED FOR THE PATIENT                                    PAGE 11 OF 11

| LINE # | NURSE STA. | ROOM BED | OV | BED COND | CLINIC CODE | HOSP SVC | ALLOWABLE PATIENT TYPES |
|---|---|---|---|---|---|---|---|
| 1 | ●CMA2 | CAD102 | O | C | | | S, D, |
| 2 | ●CMA1 | CMD157 | O | C | | | S, D, O, |
| 3 | ●CMA1 | CMD161 | O | C | | | S, D, O, |
| 4 | ●EMER | EMR001 | O | C | | | H, E, S, D, |
| 5 | ●FMF0 | FMF001 | O | C | | | H, E, S, D, |
| 6 | ●MND3 | MND001 | O | C | | | H, E, S, D, |
| 7 | ●2SOU | 021402 | O | C | | | D, H, S, E, |
| 8 | ●2SOU | 021601 | O | C | | | D, I, S, E, |
| 9 | ●3WST | 031603 | O | C | SPORT | MED | S, P, I, D, |
| 10 | ●IMCU | 405-02 | O | C | | | D, I, S, E, |
| 11 | | | | | | | |
| 12 | | | | | | | |

KEY IN A NUMBER [ ] AND PRESS ENTER

● (PF14) RETURN TO PREVIOUS SCREEN
● (PF15) LIST VACANT BEDS FOR CLINIC
● PREVIOUS PAGE    ●BEGINNING

PATIENT BED SEARCH AND MANAGEMENT SYSTEM

This is a continuation application of non-provisional application Ser. No. 11/780,641 claiming priority of provisional application Ser. No. 60/820,353 filed Jul. 26, 2006, by G. D. Auker et al.

FIELD OF THE INVENTION

This invention concerns a patient bed search system based on patient clinical and non-clinical requirements of a patient and a request to allocate a bed for the patient.

BACKGROUND OF THE INVENTION

In the U.S. healthcare environment, in which hospitals may operate near, at, or sometimes over capacity, beds are a vital resource to be managed. In order to find an appropriate bed for a patient requires specific knowledge concerning current status of beds in a facility and also requires manual matching of clinical and non-clinical needs of a patient with appropriate beds. In many facilities, a variety of factors contribute to delays in recording patient discharges and transfers, so the most appropriate bed for a given patient may be one that is not recorded in the healthcare information system as being available. It is desirable a care provider knows the specific attributes of individual beds, availability of the individual beds and the specific clinical and non-clinical needs and requests of a patient and care providers involved.

Known healthcare information systems typically provide a list of unoccupied beds without associated attributes. Therefore in known systems, if a user wishes to locate a bed with specific characteristics, both manual intervention and predetermined knowledge on the part of the user is needed. Further, known systems fail to provide an automated process of matching patient clinical and non-clinical needs with the known available beds and fail to support comprehensive healthcare workflow involving patient placement. Known systems are also typically unable to automatically prioritize and select available beds based on patient needs and are reliant on user skill and experience and do not improve the selection of beds using automated intelligent bed searches and generation of prioritized lists of available beds for matching patient needs with bed availability. In known systems, a user needs to manually determine clinical and non-clinical needs by asking a patient and reviewing stored patient information. Known systems involve manual collection of data, personal knowledge of attributes of available beds and may involve contacting a nurse responsible for a candidate bed to acquire attribute information.

The number of steps involved in known manual patient bed management systems varies based on user personal knowledge of individual bed status and characteristics in a facility and the number of phone calls that need to be made to acquired such information. Known systems involve a user in manually recording patient bed requirements and manually matching attributes of a bed with a patient bed requirements. A system according to invention principles addresses these burdens, deficiencies and related problems.

SUMMARY OF THE INVENTION

The inventors have advantageously recognized it may be desirable to assign a patient to a bed that is currently occupied by second patient whose discharge or transfer from that bed is pending. An automated search system uses data indicating clinical and non-clinical needs of a patient to provide a ranked list of candidate beds, status of beds and availability of a specific type of bed having a particular clinical attribute, using a score value derived using configurable rules for comparing patient requirements with bed characteristics. A patient bed search system includes at least one repository including bed information for multiple beds in a healthcare facility comprising multiple clinical attributes including current availability for individual beds of the multiple beds. A bed management processor automatically employs the bed information in providing data representing a candidate list of beds for a particular patient in response to clinical and non-clinical requirements associated with the particular patient and a request to allocate a bed for the particular patient. A user interface generates data representing at least one display image presenting the candidate list of beds for a particular patient.

DETAILED DESCRIPTION OF THE INVENTION

Figure 1:
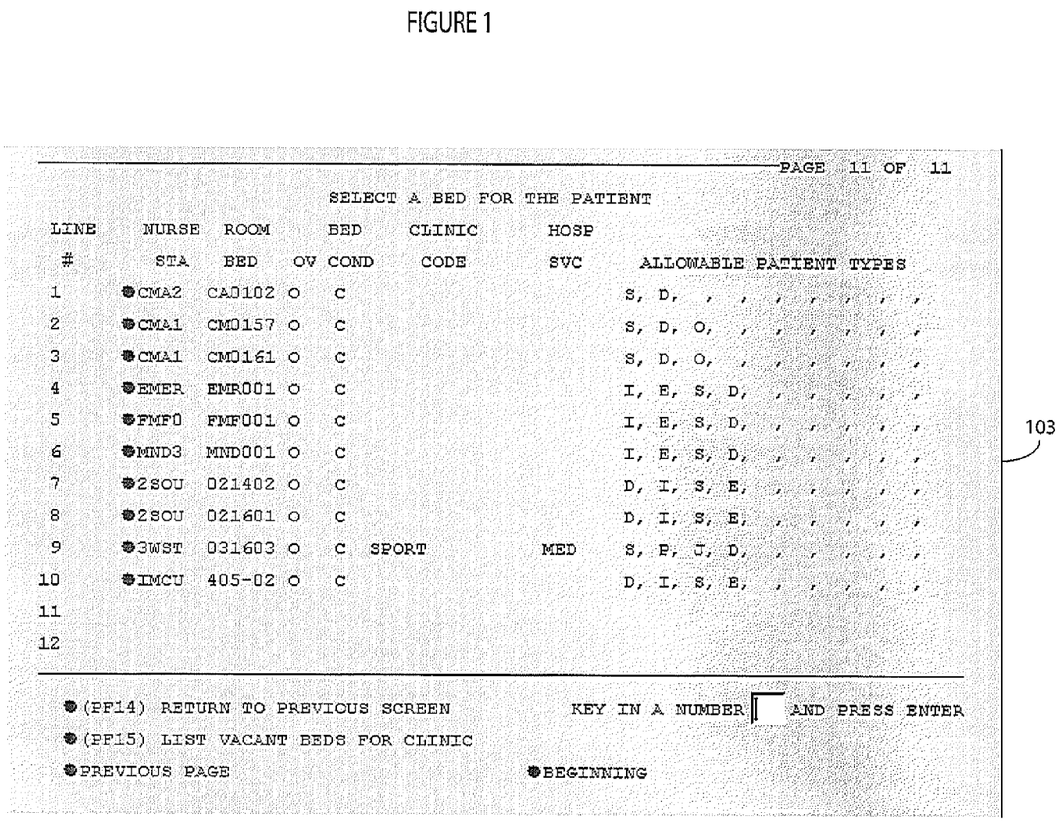
FIG. 1 shows a prior art user interface display image illustrating bed status.

FIG. 1 shows prior art user interface display image 103 illustrating bed status. Display image 103 indicates beds that are currently not occupied by other patients. Image 103 further indicates whether or not individual beds are clean, together with the clinic and hospital service where the bed is located and patient types that individual beds are able to accept as determined by a hospital. Image 103 fails to show detailed clinical and non-clinical attributes of any beds and does not support automatic matching of clinical and non-clinical needs of a patient.

Figure 2:
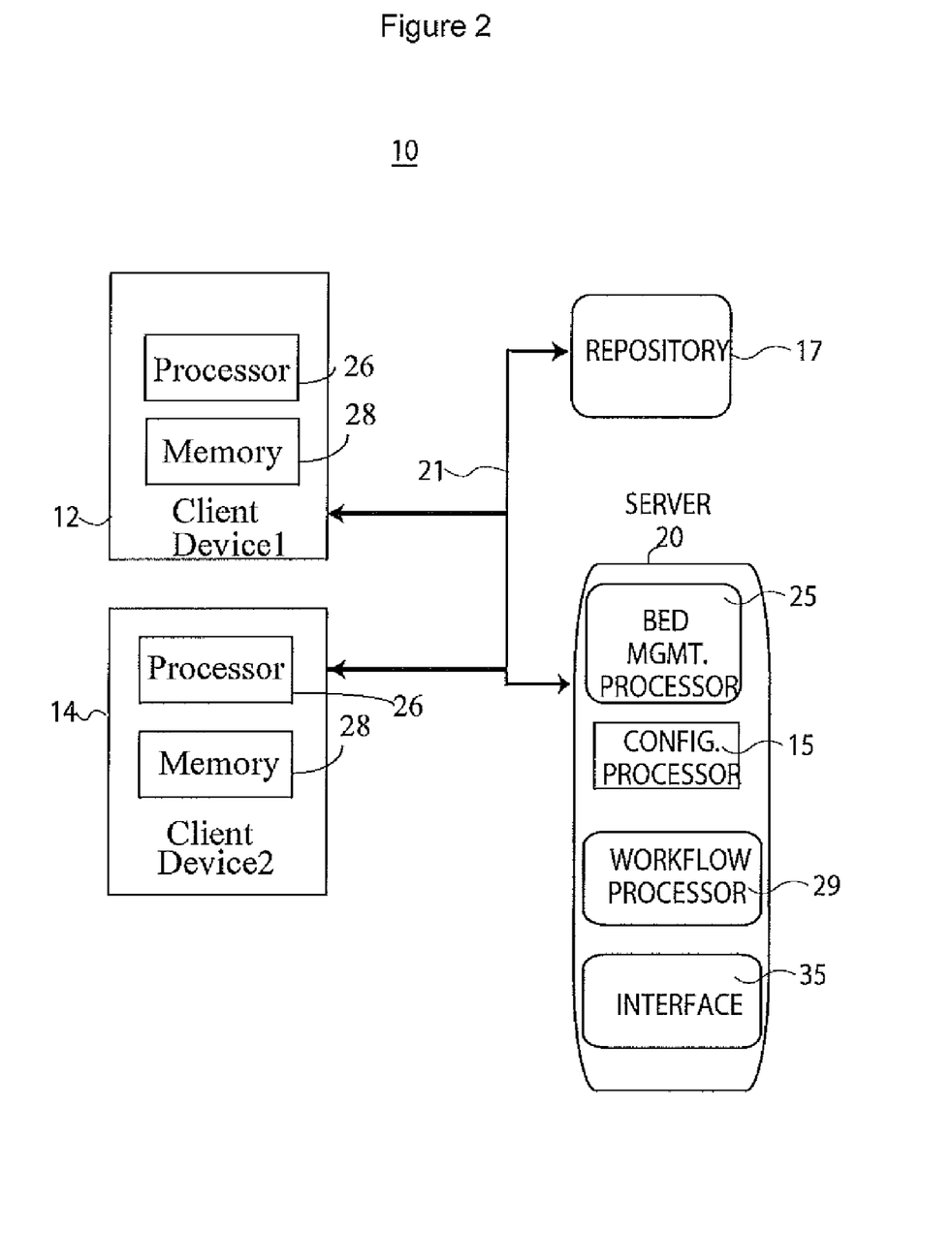
FIG. 2 shows a patient bed search and management system, according to invention principles.

In contrast, system 10 according to invention principles and illustrated in FIG. 2 automates selection and prioritization of appropriate beds for patient placement using data indicating clinical and non-clinical needs of a patient. System 10 supports a search that displays optimum available beds that match requested attributes and sorts a search result candidate list of beds so that the best and closest match is ranked with the closest match being first. System 10 provides a display image that also shows various attributes of the search so that a user is able to see detailed matching characteristics in the search results. The system uses data indicating clinical and non-clinical needs of a patient to provide a ranked list of candidate beds, status of beds and availability of a specific type of bed having a particular clinical attribute, using a score value derived using configurable rules for comparing patient requirements with bed characteristics. System 10 also facilitates automatically determining whether a bed with a less than perfect score value may be made suitable by supplementing the inherent characteristics of a bed by other means. For example, search results for a patient needing telemetry may not return any perfect matches if no beds supporting telemetry are available. However, a bed that meets the other patient clinical requirements may be made a perfect match by using portable telemetry equipment, if such equipment is determined by system 10 to be available. System 10 also automatically determines whether a bed with a less than perfect score value is clinically appropriate, even though patient preferences cannot be accommodated and identifies suitable beds that are currently occupied, but with current occupants are pending discharge or transfer.

A processor, as used herein, operates under the control of an executable application to (a) receive information from an input information device, (b) process the information by manipulating, analyzing, modifying, converting and/or transmitting the information, and/or (c) route the information to an output information device. A processor may use, or comprise the capabilities of a controller or microprocessor, for example. The processor may operate with a display processor or generator. A display processor or generator is a known element for generating signals representing display images or portions thereof. A processor and a display processor may comprise a combination of hardware, firmware, and/or software.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A user interface (UI), as used herein, comprises one or more display images, generated by a display processor and enabling user interaction with a processor or other device and associated data acquisition and processing functions. The UI also includes an executable procedure or executable application. The executable procedure or executable application conditions the display processor to generate signals representing the UI display images. These signals are supplied to a display device which displays an image for viewing by the user. The executable procedure or executable application further receives signals from user input devices, such as a keyboard, mouse, light pen, touch screen or any other means allowing a user to provide data to a processor. The processor, under control of an executable procedure or executable application manipulates the UI display images in response to the signals received from the input devices. In this way, the user interacts with a display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. Workflow comprises a sequence of tasks performed by a device or worker or both.

An object or data object comprises a grouping of data, executable instructions or a combination of both or an executable procedure.

A workflow processor, as used herein, processes data to determine tasks to add to a task list, remove from a task list or modifies tasks incorporated on, or for incorporation on, a task list. A task list is a list of tasks for performance by a worker or device or a combination of both. A workflow processor may or may not employ a workflow engine. A workflow engine, as used herein, is a processor executing in response to predetermined process definitions that implement processes responsive to events and event associated data. The workflow engine implements processes in sequence and/or concurrently, responsive to event associated data to determine tasks for performance by a device and or worker and for updating task lists of a device and a worker to include determined tasks. A process definition is definable by a user and comprises a sequence of process steps including one or more, of start, wait, decision and task allocation steps for performance by a device and or worker, for example. An event is an occurrence affecting operation of a process implemented using a process definition.

A Workflow Management System is a software system that manages processes. It includes a process definition function that allows users to define a process that should be followed, an Event Monitor, which captures events from a Healthcare Information System and communicates the results to the Workflow Management System. A processor in the Management System tracks which processes are running, for which patients, and what step needs to be executed next, according to a process definition. The Management System includes a procedure for notifying clinicians of a task to be performed, through their worklists and a procedure for allocating and assigning tasks to specific users or specific teams. A document or record comprises a compilation of data in electronic form and is the equivalent of a paper document and may comprise a single, self-contained unit of information.

FIG. 2 shows an automated patient bed search and management system 10. Bed search and management system 10 includes client devices (workstations) 12 and 14, repository 17 and server 20 bidirectionally communicating via network 21. Repository 17 (comprising one or more local or remote databases) includes bed information for multiple beds in a healthcare facility comprising multiple clinical attributes including current and pending availability for individual beds of the multiple beds. Server 20 includes bed management processor 25 for automatically employing the bed information in providing data representing a candidate list of beds for a particular patient in response to clinical and non-clinical requirements associated with the particular patient and in response to a request to allocate a bed for the particular patient. A user interface in processor 26 in workstations 12 and 14 generates data representing at least one display image presenting the candidate list of beds for a particular patient. The clinical requirements associated with the particular patient are related to at least one of, (a) patient gender, (b) whether a patient has a contagious medical condition, (c) if a patient has a contagious medical condition, whether a patient can be cohorted (i.e., can share a room with another patient having the same contagious medical condition per facility infection prevention and control policies), (d) whether a patient needs telemetry monitoring, (e) whether a patient needs a particular air or pressure environment, (f) whether a patient needs isolation and (g) whether a particular bed type or bed location is required. The non-clinical requirements associated with the particular patient are related to at least one of, a preference for patient privacy, patient entertainment or communication preferences and patient room type or room location preferences.

The multiple clinical attributes including current and pending availability for an individual bed comprise, (a) whether a bed is suitable for patients of a specific gender, (b) whether a bed is suitable for one or more particular contagious medical conditions, (c) whether a bed supports patient telemetry monitoring, (d) whether a room provides a particular air or pressure environment, (e) whether a room supports patient isolation and (f) a particular bed type or bed location, for example.

System 10 automatically takes into account both patient clinical and non-clinical needs in performing a search of patient care beds of a healthcare provider organization to determine the most suitable bed for a patient. Data indicating the clinical and non-clinical needs determined by a patient, care provider and healthcare provider organization is automatically (or at least partially manually in one embodiment) provided to bed management processor 25. Bed management processor 25 provides data representing a ranked candidate list of beds for a particular patient by ranking identified beds using identified clinical and non-clinical requirements associated with the particular patient and ranking the candidate list of beds in response to scores, associated with individual clinical and non-clinical requirements and indicating relative significance of the clinical and non-clinical requirements. Bed management processor 25 applies predetermined rules in assigning the scores indicating relative significance used in identifying and ranking candidate beds. Bed management processor 25 assigns individual pre-determined scores to corresponding individual satisfied search criteria and combinations of satisfied search criterion values and derives a cumulative score from the assigned individual scores and uses the cumulative score to rank identified beds.

Bed management processor 25 provide results comprising a ranked list of beds presented in descending order by score, for example, so the most appropriate bed for the patient is listed at the top. A bed score is derived based on configurable rules that are applied in comparing patient requirements with bed characteristics. This enables a user to automatically and expeditiously find the most appropriate bed for a patient from a candidate list and to assign a patient to the bed. The bed search is also useful in providing a display image view indicating a current bed status within a health care facility. For example, a search determines how many of a certain type of bed such as a bed having a certain clinical attribute exist within a health care facility. Workflow processor 29 comprising a workflow engine automatically uses information indicating needs of the patient and the known attributes and availabilities of the beds to substantially immediately initiate performance of tasks (e.g., admit and assign a patient to a bed, initiate providing supplementary medical equipment to a room) thereby improving efficiency by performing workflow steps that would otherwise be performed manually.

Interface 35 of system 10 automatically (without user intervention) acquires clinical and non-clinical information for individual beds within a healthcare provider organization from a Healthcare Information System (HIS) or from interrogating multiple different sources. The acquired information may be specific to a bed or to a room housing the bed, nurse station, unit, etc, where the bed is located. The acquired information may comprise any information that a healthcare provider organization configures system 10 via processor 15 to recognize as an attribute of a bed. Clinical and non-clinical attributes of a bed are defined by a healthcare provider organization responsible for the beds using configuration processor 15. A clinical attribute may indicate a bed is bariatric-capable or a thermal sand bed, for example. A non-clinical attribute may indicate a bed has an Internet connection available or is appropriate for VIPs (Very Important Persons). Once data indicating attributes of a bed is automatically acquired by interface 35 and stored in repository 17, bed management processor 25 initiates generation of a User Interface (UI) display image for display on workstation 12, for example, enabling a user to select from bed attributes pre-configured by a healthcare provider organization. A display image enables a user to apply sorting and filtering criteria to tailor a resulting candidate bed list to needs. Bed management processor 25 includes a search engine employing specific clinical and non-clinical attributes pre-configured by a healthcare provider organization and patients to improve a bed search, selection and allocation workflow using an automated process.

The clinical information, bed definition information and patient information (including non-clinical information supplied by the patient) already known and stored in repository 17, is automatically taken into account for a bed search. In one embodiment, system 10 replaces multiple manual workflow steps with a single automatically performed workflow step. Specifically, a search for the most appropriate bed is a one step search instead of an entirely manual process involving multiple healthcare providers with specific knowledge of the attributes and state of beds within their individual corresponding areas. System 10 also facilitates locating appropriate beds for infectious patients and maximizes bed usage capacity. Many hospitals have a shortage (or complete lack) of specialized isolation rooms for infectious patients, and therefore occasionally place such patients in semi-private rooms. With certain infectious conditions (for example, methicillin-resistant *Staphylococcus aureus,* or MRSA), it is clinically acceptable to create cohorts of patients with the same condition (and no others), and to place these patients in the same room. System 10 supports this task and contributes to the avoidance of patient hazards by facilitating the consolidation of infectious patients into as few semi-private rooms as possible.

System 10 operates in conjunction with a Hospital Information System (HIS) that stores bed requests (containing patient bed requirements), information about patients who already occupy beds, and bed definitions. Bed requests are created during ADT (Admission/Discharge/Transfer) activities, at the time of pre-admission or when preparing for a pending transfer, for example. A bed definition includes the specification of characteristic of a bed that are significant in bed management such as characteristics potentially satisfying patient clinical requirements for bed placement. Bed characteristics may be related to specialized usage (such as, an observation bed, or overflow bed), its location (such as near a nurse station, or on the first floor), or its specialized capabilities (such as a bariatric bed or thermal sand bed). An HIS presents patient bed requests to bed administration personnel via a worklist of patients needing bed assignments. As bed administration personnel address an individual bed request, patient bed requirements are automatically provided to system 10 and stored in repository 17 and used to populate search parameters. In one embodiment a display image on workstation 12 enables a user to revise default parameter values before a search is initiated. When a user initiates a search, system 10 automatically compares parameters to characteristics of individual beds.

Figure 3:
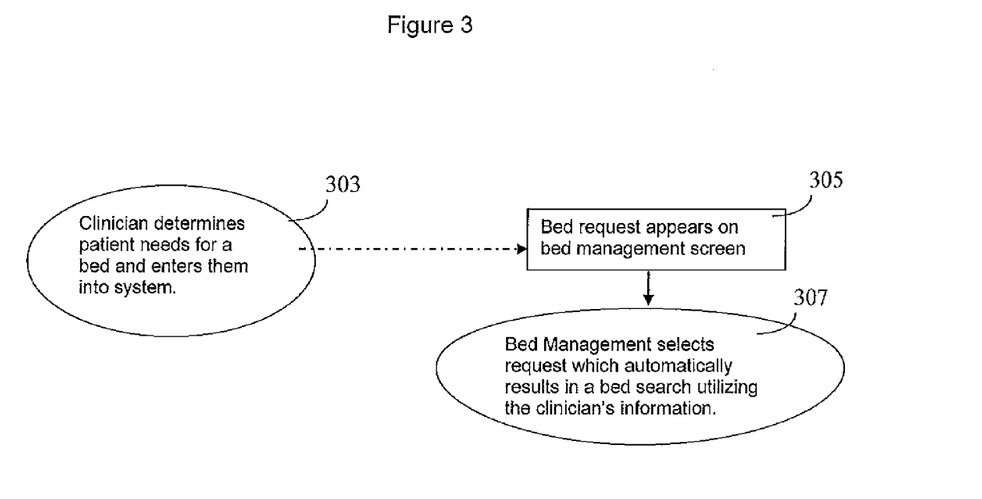
FIG. 3 shows an overview flowchart of a process employed by a patient bed search and management system, according to invention principles.

FIG. 3 shows an overview flowchart of a process employed by patient bed search and management system 10. In step 303 a user determines patient needs for a bed and enters them in system 10 using workstation 12 for storage in repository 17.

Figure 6:
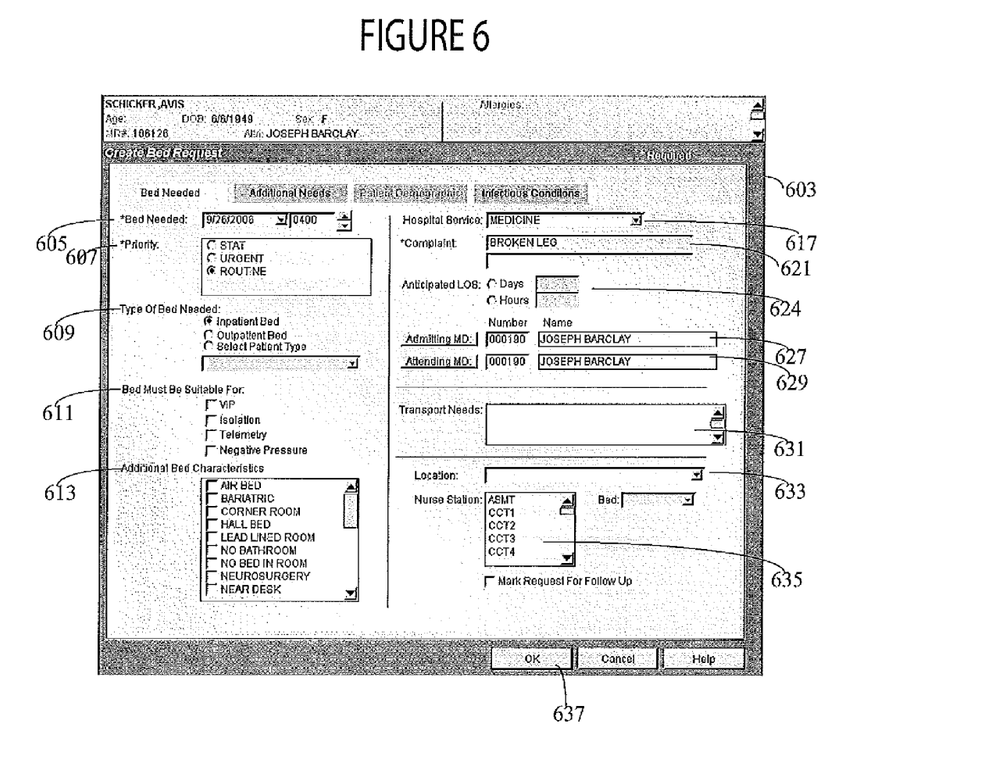
FIG. 6 shows a user interface display image enabling a user to initiate a request for a bed, which is auto-populated from the patient's record, according to invention principles.

FIG. 6 shows user interface display image 603 enabling a user to initiate a request for a bed based on clinical and non-clinical attributes. A user enters a date and time a bed is needed 605, a bed request priority 607 (e.g., urgent, routine), a type of bed needed 609 (e.g., inpatient, outpatient, based on patient type) and bed characteristics 611 (e.g., suitable for isolation, telemetry, a VIP, negative pressure environment), additional bed characteristics 613 (e.g., air bed, bariatric bed, corner room, hall bed, lead lined room, no bathroom, room without bed, neurosurgical). A user further selects associated parameters including, a hospital service 617, a complaint 621, anticipated length of stay 624, admitting physician 627, attending physician 629, transport needs 631, bed location 633 and nurse station 635. Upon selection of the parameters a user enters them by selecting button 637 into system 10 via interface 35 for storage in repository 17.

In an alternative embodiment the bed request information of image 603 is automatically derived in response to data indicating admission or a request for-admission and indicating nature of a patient medical condition and other patient data acquired from a patient medical record or other sources including demographic data (gender, age, height, weight, for example). This is done based on a predetermined database of information associating medical condition, demographic data and expected bed type and also optionally, predetermined physician and patient preferences.

Figure 4:
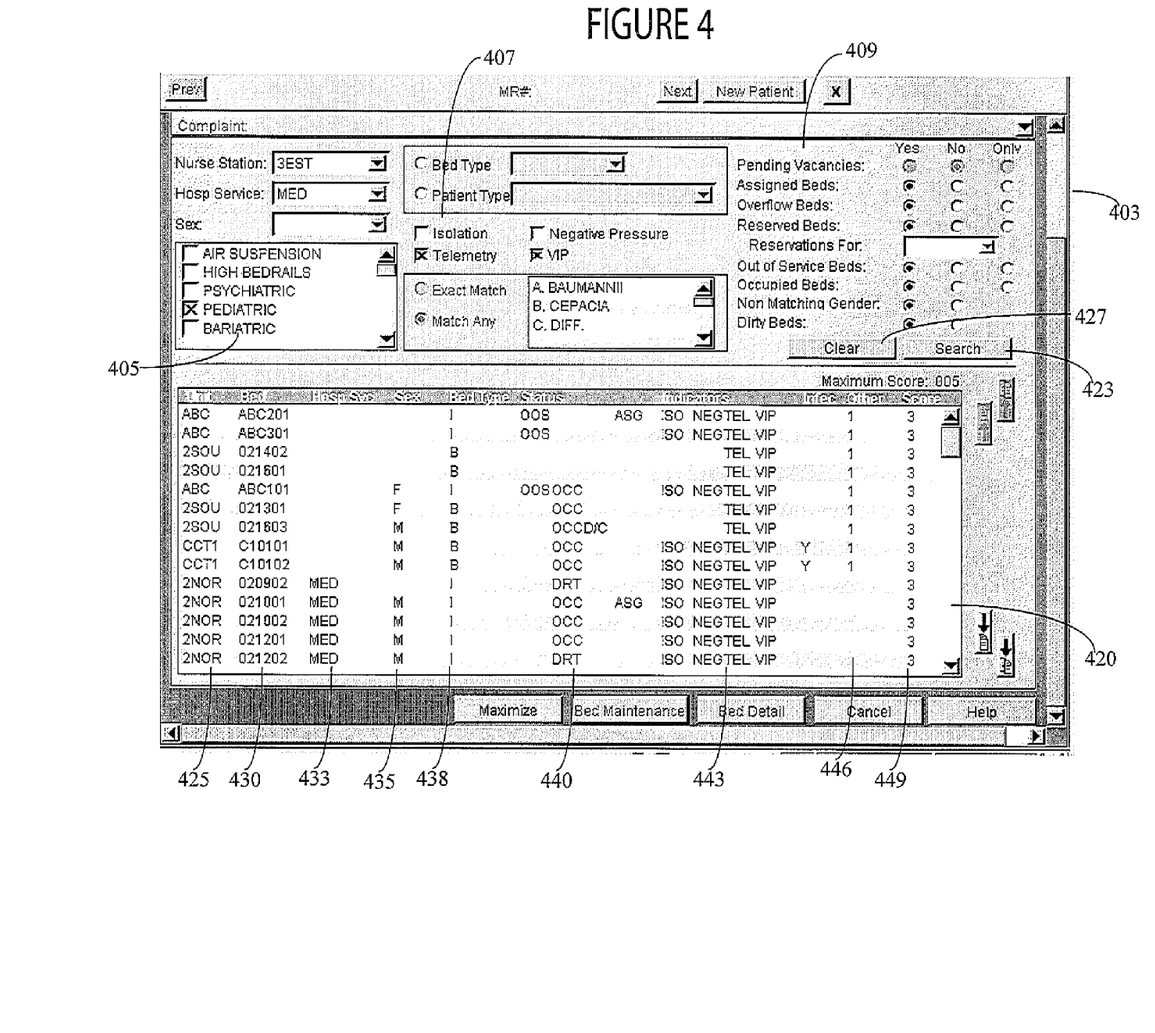
FIG. 4 shows a user interface display image enabling a user to initiate a bed search for a patient employing user entered clinical and non-clinical attributes, according to invention principles.

In step 305 (FIG. 3) in response to the user bed request data entry via image 603 (FIG. 6), a bed request appears in a user interface display image presented on workstation 14, for example. FIG. 4 shows user interface display image 403 enabling a user to initiate a bed search for a patient employing user entered clinical and non-clinical attributes. Bed management processor 25 (FIG. 1) incorporates a bed search engine, responsive to predetermined and adaptively modified rules, that identifies appropriate bed assignments for a patient, based on patient clinical and non-clinical requirements. A search is performed to provide results filtered based on user selectable options including, bed housekeeping status, occupancy status or in-service status, for example. Display image 403 enables a user to provide clinical information as well as non-clinical information in selectable option list 405 and selectable buttons 407. Option list 405 includes non-clinical attributes as well as additional user determined clinical attributes that are selectable as search criteria. List 405 contains a comprehensive list of bed attributes a hospital requires. The same attributes are available for selection in the bed request form of FIG. 6. Further, bed management processor 25 automatically selects bed attribute items in list 405 as search criteria if they are selected items in the bed request of display image 603. Bed management processor 25 in step 307 (FIG. 3) automatically selects data representing the bed request and automatically initiates a search of data in repository 17 using the user entered bed request information. The selectable attributes of list 405 are configurable by a user employing processor 15. A user is able to supply as many or as few attributes as desired to be associated with beds within a healthcare provider organization, for example.

Further, a user is able to acquire search results filtered based on filtering options in column 409. A search may provide filtered results that must include, exclude or only include beds having selected filtering options 409. The filtering options 409 indicate, for example, that search results include, beds for which there are pending vacancies, already assigned beds, overflow beds, reserved beds, out of service beds, occupied beds, dirty beds and beds for a patient of different gender. Filtering options 409 advantageously enable a user to broaden a search to include, for example, dirty, occupied, or out-of-service beds in search results. A user clears search options via selection of button 427 and initiates a search based on entered parameters shown in image 403 by selecting button 423.

Box 420 presents search results comprising data indicating available beds obtained based on at least one of the search criteria as well as based on the filter criteria selected and shown in image 403. The beds identified in the search results in box 420 are sorted and ranked in descending order according to a score value in column 449. A score value for an individual bed is determined using user configured hospital specific (or default) rules, for example. The piles determine a number of points to add to a score of an individual bed that qualifies for a search result list based on a specific data element or data element value. For example, a hospital may specify that an exact match for a search criterion indicating a bed is desired in a particular nursing unit contributes 25 points to a bed score, or that an exact match for a search criterion indicating a clinical service is desired contributes 15 points. Further, particular search parameters are used to evaluate summary information concerning a room in which a candidate bed is located, rather than information about the bed itself. For example, a room may be designated for patients of one gender, or a room may be designated as an MRSA room if it houses at least one MRSA patient. This room associated information is also automatically associated by bed management processor 25 with beds located in a room concerned. So an unoccupied bed in an MRSA room is automatically designated an MRSA bed and is identified as a candidate bed for a patient who requires MRSA appropriate accommodation.

System 10 also supports the creation and use of more complex rules to accommodate situations where a match for a search criterion is more or less significant based on a specific score value. For example, a hospital may define multiple rules that govern a bed score when a clinical service is used as a search criterion. Therefore, for example, a match identifying a Critical Care clinical service for a search criterion requiring a clinical service may contribute 25 points to a bed score, while a match identifying a surgical clinical service for a search criterion requiring a clinical service may contribute 10 points to a bed score. Bed management processor 25 also uses complex rules that reference multiple search parameters. In an example, a nursing unit in a hospital provides a primary, and one or more secondary services, and the hospital desires, whenever possible, to direct patients requiring a primary service to this nursing unit. Therefore, rules are generated using system 10, to assign one score to a bed if a requested nursing unit is 3 West and the required service is primary (e.g., Surgical) but a different score for the same bed if the requested nursing unit is 3 West and the required service is secondary (e.g., Medical).

Bed management processor 25 also enables creation and use of complex rules (using algebraic and logical operators, for example) referring to multiple data elements. Such rules enable a pair of data elements or expressions to be related via operators including AND, OR, EXCLUSIVE OR, MUST, MUST NOT etc. As an example a rule may find beds and allocate a score satisfying the expression: if nursing unit is 3 West and a clinical service is medical, add n to a qualifying bed score if it is located on 3 West and supports medical service. A different rule may find beds and allocate a score satisfying the expression: if "patient requires isolation?" is "true" or "patient has MRSA" is "true," add n to a qualifying bed score if it is defined as appropriate for isolation or if it is located in an MRSA room. Score value processing rules enable a hospital to determine which search parameters and search parameter values are the most significant. Bed management processor 25, in response to the rules, determines which beds are the most appropriate for any set of search inputs. The score processing rules are prioritized in groups in order (highest priority to lowest) and may include, complex rules that evaluate multiple data elements, rules that test for multiple values of the same data element, simple rules that test for one value of one data element and simple rules that test for an exact match (but no specific value) of one data element, for example. Within these groups, individual rules are prioritized by user (or default) configuration.

Bed score processing rules may overlap, as in the following first and second rules, where both rules refer to a medical clinical service. First rule: if the nursing unit search parameter is "3 West" and the clinical service search parameter is "medical," add 7 to a qualifying bed score if its characteristics match. Second rule: if the clinical service search parameter is "medical," add 3 to a qualifying bed score if its clinical service characteristic matches. Further, in order to prevent duplicate scoring for overlapping rules, a lower priority rule is not applied to a query if it overlaps a higher priority rule that is indicated as being "true". The search results indicated in box 420 of the search illustrated in image 403 show the closest matching beds have a score of 3 out of a maximum of 5. Bed management processor 25 advantageously presents search results in box 420 indicating bed and bed associated characteristics. These characteristics include, hospital unit of the bed 425, bed identifier 430, hospital service 433, gender 435, bed type indicator (e.g., bariatric B) 438, status (e.g., occupied or assigned for occupancy) 440, additional indicators (e.g., indicating isolation, negative pressure, telemetry, VIP) 443, other user definable indicator 446 and score value 449.

Figure 5:
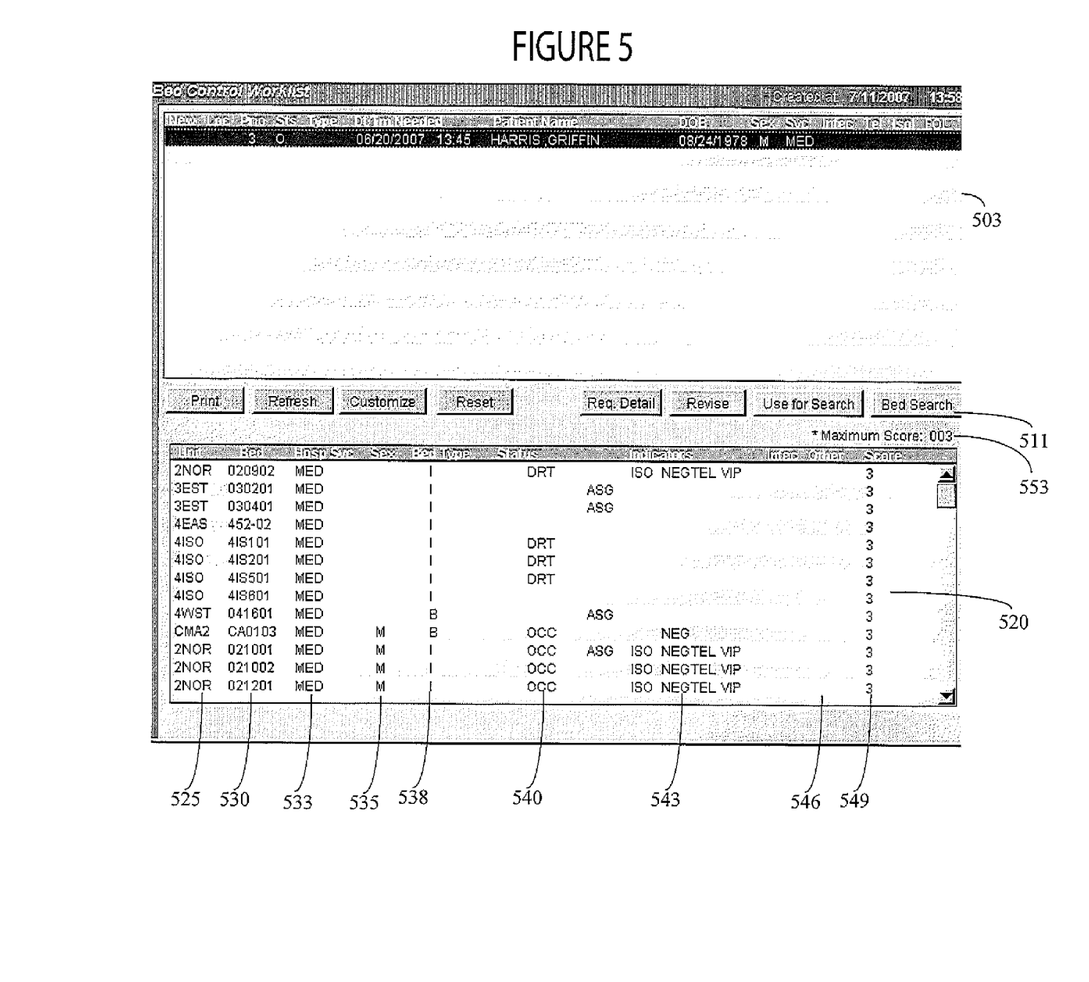
FIG. 5 shows a user interface display image enabling a user to view a list of outstanding electronic bed requests from which he can select one and initiate a bed search for a patient, according to invention principles.

FIG. 5 shows user interface display image 503 enabling a user to initiate a bed availability search for a patient employing auto-populated user entered clinical and non-clinical attributes (e.g., auto-populated using bed attributes acquired from the bed request of display image 603). The bed search criteria in this embodiment are automatically derived by bed management processor 25 and used to populate bed search image 503. The bed search criteria are automatically derived by bed management processor 25 from a patient admission form or corresponding HL7 (for example) transaction message, a healthcare information system, physician or user entered scheduled appointment information or acquired bed request data entered via an image exemplified in FIG. 6. The bed search criteria are automatically (or manually in another embodiment) derived from information including clinical and non-clinical information known at the time a bed was requested for the patient. The bed search criteria are automatically used in a bed search in response to a user selecting a request for a bed.

In response to a user selecting a request for a bed known to the system and selecting Bed Search button 511, bed management processor 25 initiates a bed search of data in repository 17 to automatically find beds that best match determined clinical and non-clinical needs of a patient. The search results indicated in box 520 of the search illustrated in image 503 show the closest matching beds have a score of 8 out of a maximum of 11 (item 553). Bed management processor 25 advantageously presents search results in box 520 indicating bed and bed associated characteristics. These characteristics (in a similar manner to FIG. 4) include, hospital unit of the bed 525, bed identifier 530, hospital service 533, gender 535, bed type indicator (e.g., bariatric B) 538, status (e.g., occupied or assigned for occupancy) 540, additional indicators (e.g., indicating isolation, negative pressure, telemetry, VIP) 543, other user definable indicator 546 and score value 549.

The patient bed requirements matched rules that total 11 possible points. This maximum score 553 is displayed, for easy reference, in close proximity to scores for individual beds that qualify for the search results list. The bed with the highest score matched rules that contributed 8 of the possible 11 points as indicated in column 549.

A user is able to compare characteristics of a requested bed with characteristics identified as matching indicated in box 520 and determine whether the bed is suitable or can be made suitable. Any bed can be selected from the available list shown in box 520. System 10 provides that clinical and non-clinical needs of a patient and attributes and current status and pending status of a candidate bed are substantially immediately known. A user is able to select a bed without any further manual steps. Bed management processor 25 initiates generation of display image 503 automatically in response to data in the form of a bed request supplied by a clinician familiar with the needs of a patient.

Bed management processor 25 automatically takes into account known clinical and non-clinical needs of a patient when searching for a bed. Candidate beds identified in search results are ranked based on a score determined by processor 25 derived using hospital-defined rules and displayed in ranked order such that the highest scoring beds are displayed first. The score is derived using hospital-determined clinical and non-clinical attributes for beds in a facility and are stored in repository 17. The system supports a bed search accommodating beds assigned to individual infectious patients or groups of infectious patients and minimizes a risk of multiple semi-private rooms being assigned a single occupant.

Figure 7:
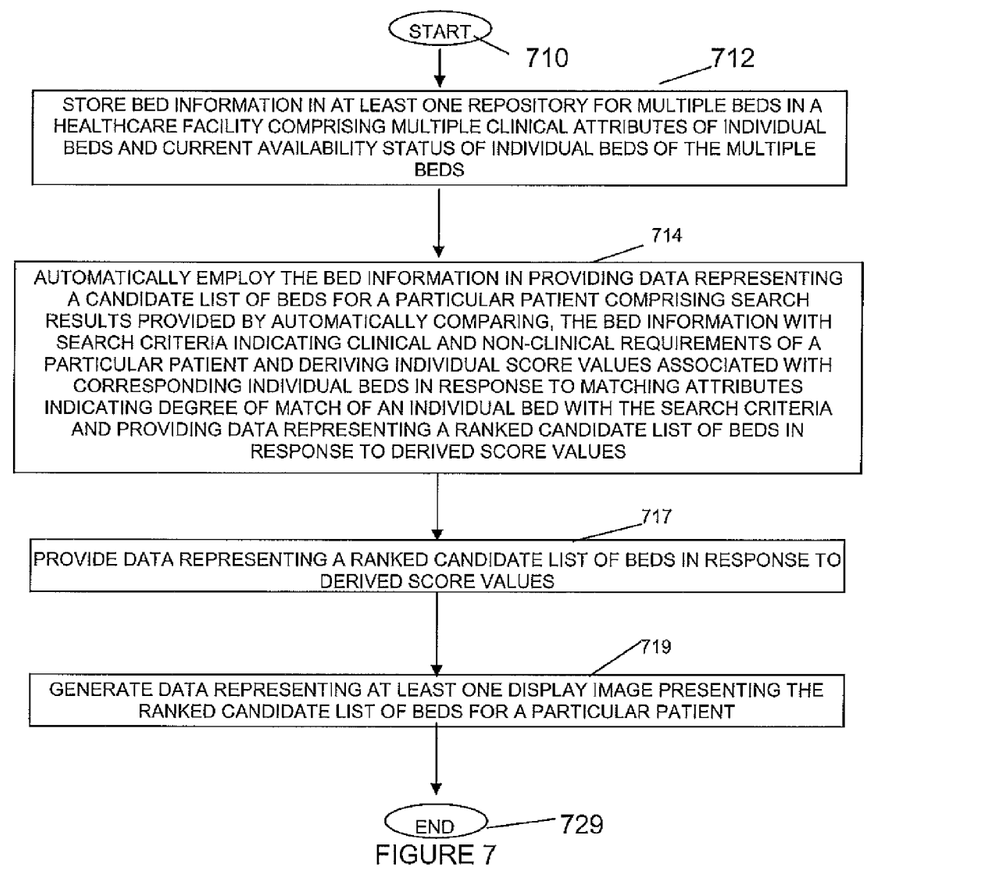
FIG. 7 shows a flowchart of a process performed by a patient bed search and management system, according to invention principles.

FIG. 7 shows a flowchart of a process performed by patient bed search and management system 10. The steps of FIG. 7 may be performed automatically. In step 712 following the start at step 710, interface 35 of system 10 automatically acquires and stores bed information in at least one repository (e.g., repository 17) for multiple beds in a healthcare facility comprising multiple clinical attributes of individual beds and current availability status of individual beds of the multiple beds. In step 714, bed management processor 25 automatically employs the bed information in providing data representing a candidate list of beds for a particular patient. The candidate list of beds comprises search results provided by initiating a search and automatically comparing, the bed information with search criteria indicating clinical and non-clinical requirements of a particular patient and deriving individual score values associated with corresponding individual beds in response to matching attributes indicating degree of match of an individual bed with the search criteria. The clinical and non-clinical requirements of the particular patient are acquired from a request to allocate a bed for the particular patient. Bed management processor 25 computes individual scores in response to predetermined rules that define scores for possible combinations of search criteria and search criterion values. Bed management processor 25 also determines a highest attainable cumulative value for comparison with a cumulative value derived for the ranked identified beds.

Bed management processor 25 automatically employs the bed information in providing data representing a candidate list of beds for a particular patient in response to received clinical and non-clinical requirements associated with the particular patient stored in repository 17 in response to a patient specific condition. Further, the patient specific condition includes a bed assignment request command by a healthcare worker and the received clinical and non-clinical requirements associated with the particular patient comprise patient specific context information including the clinical and non-clinical requirements using data received from an executable application. Bed management processor 25 automatically populates bed search criteria in response to the bed assignment request command and uses the search criteria in deriving the data representing the candidate list of beds for the particular patient.

A sorting processor (not shown) in bed management processor 25 in step 717 provides data representing a ranked candidate list of beds in response to derived score values. A user interface in workstation 12 (or in another embodiment in processor 25) in step 719 generates data representing at least one display image presenting the ranked candidate list of beds for a particular patient. The at least one display image includes bed status, bed type indicator, hospital unit of the bed, bed identifier and hospital service indicator. The at least one display image also incorporates an indicator indicating bed attributes including one or more of isolation, negative pressure, telemetry, and for VIP patients. Further, a display image enables user entry of search criteria identifying clinical and non-clinical requirements associated with the particular patient. The process of FIG. 7 terminates at step 729.

The system and processes of FIGS. 2-7 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. Systems 10 may be used with different hospital information systems (HISs) and patient management systems that have processing needs to manage patients and patient beds and is usable for multiple hospital departmental systems, such as Emergency Department Information Management systems that interface with an HIS. The system provides a workflow automatically associating patient needs with bed attributes that would otherwise require complex skills and experiences thereby advantageously reducing the need for such skill and experience. The processes and applications may in alternative embodiments, be located on one or more (e.g., distributed) processing devices accessing a network linking the elements of FIG. 2. Further, any of the functions and steps provided in FIGS. 1-7 may be implemented in hardware, software or a combination of both and may reside on one or more processing devices located at any location of a network linking the elements of FIG. 2 or another linked network including the Internet.

What is claimed is:

1. A patient bed search system implemented by at least one processing device, comprising:
   at least one repository including bed information for a plurality of beds in a healthcare facility, said bed information comprising a plurality of clinical attributes of individual beds and current and pending availability status of individual beds of said plurality of beds;
   a bed management processor for automatically employing said bed information in providing data representing a candidate list of beds for a particular patient by initiating a search and by assigning individual predetermined scores to corresponding individual satisfied search criteria and combinations of satisfied search criterion values and deriving a cumulative score from the assigned individual scores and using said cumulative score to rank identified beds and provide said candidate list of beds; and
   a user interface for generating data representing at least one display image presenting said candidate list of beds for a particular patient.

2. A system according to claim 1, wherein
   said bed management processor automatically employs said bed information in providing data representing a candidate list of beds for a particular patient in response to clinical and non-clinical requirements associated with said particular patient and
   said clinical requirements associated with said particular patient are related to at least one of, (a) patient gender, (b) whether a patient has a contagious medical condition, (c) whether a patient having a contagious medical condition, can share a room with another patient having the same contagious medical condition, (d) whether a patient needs telemetry monitoring, (e) whether a patient needs a particular air or pressure environment, (f) whether a patient needs isolation, (g) whether a particular bed type or bed location is required and (h) whether the patient has special requirement that resides in a list defined by the facility,
   said non-clinical requirements associated with said particular patient are related to at least one of, (i) a preference for patient privacy, (ii) patient entertainment or communication preferences and (iii) patient room type or room location preferences.

3. A system according to claim 1, wherein
   said plurality of clinical attributes include current and pending availability for an individual bed comprise at least two of, (a) whether a bed is suitable for patients of a specific gender, (b) whether a bed is suitable for one or more particular contagious medical conditions, (c) whether a bed supports patient telemetry monitoring, (d) whether a room provides a particular air or pressure environment, (e) whether a room supports patient isolation and (f) a particular bed type or bed location.

4. A system according to claim 1, wherein
   said bed management processor automatically employs said bed information in providing data representing a candidate list of beds for a particular patient in response to clinical and non-clinical requirements associated with said particular patient and
   said bed management processor indicates relative significance of said clinical and non-clinical requirements.

5. A system according to claim 4, wherein
   said bed management processor applies predetermined rules in indicating relative significance of said clinical and non-clinical requirements.

6. A system according to claim 1, wherein
   said bed management processor automatically employs said bed information in providing data representing a candidate list of beds for a particular patient in response to clinical and non-clinical requirements associated with said particular patient and by comparing said bed information with said clinical and non-clinical requirements, in response to user command.

7. A system according to claim 1, wherein
   said bed management processor computes assigned individual scores in response to predetermined configurable rules that define scores for possible combinations of search criteria and search criterion values.

8. A system according to claim 4, wherein
   said bed management processor determines a highest attainable cumulative value for comparison with a cumulative value derived for said ranked identified beds.

9. A system according to claim 1, wherein
said at least one display image enables user entry of search criteria identifying clinical and non-clinical requirements associated with said particular patient and
said bed management processor providing data representing a ranked candidate list of beds for a particular patient by ranking identified beds by identifying clinical and non-clinical requirements associated with said particular patient and ranking said candidate list of beds in response to scores assigned to corresponding individual satisfied search criteria and combinations of satisfied search criterion values.

10. A system according to claim 1, wherein
said bed management processor automatically employs said bed information in providing data representing a candidate list of beds for a particular patient in response to received clinical and non-clinical requirements associated with said particular patient in response to a patient specific condition.

11. A system according to claim 10, wherein
said patient specific condition comprises a patient admission or transfer order.

12. A system according to claim 10, including
at least one repository including information identifying patient bed requirements and wherein
said patient specific condition comprises a bed assignment request command by a healthcare worker and
said bed management processor automatically employs said patient bed requirements in providing said data representing said candidate list of beds for said particular patient.

13. A system according to claim 12, wherein
said bed management processor automatically populates bed search criteria in response to said bed assignment request command and uses said search criteria in deriving said data representing said candidate list of beds for said particular patient.

14. A system according to claim 10, wherein
said received clinical and non-clinical requirements associated with said particular patient comprises patient specific context information including said clinical and non-clinical requirements using data received from an executable application.

15. A patient bed search system implemented by at least one processing device, comprising:
at least one repository including bed information for a plurality of beds in a healthcare facility comprising a plurality of clinical and non-clinical attributes of individual beds and current and pending availability status of individual beds of said plurality of beds;
a bed management processor for automatically employing said bed information in providing data representing a candidate list of beds for a particular patient by initiating a search and by assigning individual predetermined scores to corresponding individual satisfied search criteria and combinations of satisfied search criterion values and deriving a cumulative score from the assigned individual scores and using said cumulative score to rank identified beds and provide said candidate list of beds;
a sorting processor for providing data representing a ranked candidate list of beds in response to derived score values; and
a user interface for generating data representing at least one display image presenting said ranked candidate list of beds for a particular patient.

16. A system according to claim 15, wherein
said bed management processor provides data representing said ranked candidate list of beds for said particular patient by ranking identified beds by identifying clinical and non-clinical requirements associated with said particular patient and ranking said candidate list of beds in response to scores associated with individual clinical and non-clinical requirements and
said at least one display image includes bed status and bed type indicator.

17. A system according to claim 16, wherein
said at least one display image includes hospital unit of the bed, bed identifier and hospital service indicator.

18. A system according to claim 16, wherein
said bed management processor derives a cumulative score from the assigned individual scores and uses the cumulative score to rank identified beds and
said at least one display image includes an indicator indicating bed attributes including at least one of, (a) isolation, (b) negative pressure, (c) telemetry, and (d) for VIP patients.

19. A patient bed search method implemented by at least one processing device, comprising the steps of:
storing in at least one repository, bed information for a plurality of beds in a healthcare facility comprising a plurality of clinical and non-clinical attributes of individual beds and current and pending availability status of individual beds of said plurality of beds;
automatically employing said bed information in providing data representing a candidate list of beds for a particular patient by initiating a search and assigning individual predetermined scores to corresponding individual satisfied search criteria and combinations of satisfied search criterion values and deriving a cumulative score from the assigned individual scores and using said cumulative score to rank identified beds and provide said candidate list of beds; and
generating data representing at least one display image presenting the ranked candidate list of beds for a particular patient.

20. A method according to claim 19, including the step of
providing data representing a candidate list of beds for a particular patient in response to clinical and non-clinical requirements associated with said particular patient wherein
said clinical and non-clinical requirements of said particular patient are acquired from a request to allocate a bed for said particular patient and including the step of
deriving a cumulative score from the assigned individual scores and uses the cumulative score to rank identified beds.

21. A method according to claim 19, wherein
said at least one display image includes bed status and bed type indicator.

* * * * *